United States Patent [19]

Tang

[11] Patent Number: 4,526,993
[45] Date of Patent: Jul. 2, 1985

[54] CONJUGATED DIENOLS

[75] Inventor: Chaucer C. Tang, Wilmington, Del.

[73] Assignee: E. I. Du Pont de Nemours and Company, Wilmington, Del.

[21] Appl. No.: 373,703

[22] Filed: Apr. 30, 1982

[51] Int. Cl.$^3$ ............................................. C07D 317/00
[52] U.S. Cl. .................................. 549/445; 568/813; 568/884; 568/885
[58] Field of Search ................ 549/445, 447; 568/884, 568/885, 813; 560/205

[56] References Cited

U.S. PATENT DOCUMENTS

| | | | |
|---|---|---|---|
| 3,468,948 | 9/1969 | Fernholz | 260/549 |
| 3,520,839 | 7/1970 | Milligan et al. | 260/20 |
| 3,752,843 | 8/1973 | Henrick | 568/884 |
| 4,073,813 | 2/1978 | Cordier | 260/617 C |
| 4,156,791 | 5/1979 | Childs | 568/885 |
| 4,209,517 | 6/1980 | Riveria et al. | 549/445 |
| 4,293,674 | 10/1981 | Andrews | 526/327 |

OTHER PUBLICATIONS

G. F. Woods et al., J. Am. Chem. Soc., vol. 77, 1800 (1955).
R. F. Nystrom and W. G. Brown, J. Am. Chem. Soc., vol. 69, 2548, 1197 (1947).
R. F. Nystrom et al., J. Am. Chem. Soc., vol. 71, 3245 (1949).
M. S. Brown and H. Rapaport, J. Org. Chem., vol. 28, 3261 (1963).
S. W. Chaikin and W. G. Brown, J. Am. Chem. Soc., vol. 71, 122 (1949).
J. Nikawa and T. Shiba, Chem. Letters, 981 (1979).
B. C. Subba Rao, Current Science, No. 6, 218 (1961).
T. Koizumi et al., Chem. Pharm. Bull. (Japan), vol. 21, No. 2, 312 (1973).
K. Ishizumi et al., Chem. Pharm. Bull. (Japan), vol. 16, No. 3, 492 (1968).
D. S. Tarbell and N. A. Leister, J. Org. Chem., vol. 23, 1149 (1958).
L. E. Overman et al., J. Org. Chem., vol. 43, 2164 (1978).
G. W. Anderson et al., J. Am. Chem. Soc., vol. 86, 1839 (1946).
Takahashi et al., J. Org. Chem., 35 (5), 1505 (1970).
Johnstone et al., J. Chem. Soc. Chem. Communications, 354 (1978).
Raber et al., J. Org. Chem. 41 (4), 690 (1976).

*Primary Examiner*—Ethel G. Love
*Attorney, Agent, or Firm*—James A. Costello

[57] ABSTRACT

Conjugated dienols for providing cure sites to air-drying acrylic finishes are prepared from conjugated dienoic acids by conversion to an activated ester followed by sodium borohydride reduction thereof.

18 Claims, No Drawings

CONJUGATED DIENOLS

TECHNICAL FIELD

This invention relates to preparation of conjugated dienols.

BACKGROUND INFORMATION

Various carboxylic acids and derivatives thereof have been reduced to alcohols. U.S. Pat. No. 4,073,813, Cordier, is illustrative of references which teach catalytic hydrogenation of ethylenically unsaturated aldehydes to alcohols, including dienyl alcohols.

Carboxylic acid and derivatives thereof have also been reduced to alcohols with metal hydrides. It has been reported, for example, that 2,4-hexadienal has been reduced to 2,4 hexadien-1-ol (sorbyl alcohol) with sodium borohydride.

G. F. Woods et al., J. Am. Chem. Soc. volume 77, 1800 (1955), disclose lithium aluminum hydride reduction of 2,4-hexadienal to sorbyl alcohol.

R. F. Nystrom and W. G. Brown, J. Am. Chem. Soc., volume 69, 2548 (1947) describe reduction of several carboxylic acids, including sorbic acid and cinnamic acid, to alcohols using lithium aluminum hydride. The authors report that the olefinic double bonds of sorbic acid are not reduced whereas the double bond of cinnamic acid is.

R. F. Nystrom and W. G. Brown, J. Amer. Chem. Soc., volume 69, 1197 (1947) describe reduction of aldehydes, ketones, carboxylate esters, acid chlorides and acid anhydrides using lithium aluminum hydride. The esters are aromatic, mono-unsaturated or saturated. Sorboyl chloride is reduced to sorbyl alcohol.

R. F. Nystrom et al., J. Am. Chem. Soc., volume 71, 3245 (1949) describe reduction of certain aromatic or saturated aldehydes, ketones, carboxylate esters and carboxylic acids using lithium borohydride as the reducing agent.

M. S. Brown and H. Rapaport, J. Org. Chem., volume 28, 3261 (1963) describe reduction of methyl esters of various carboxylic acids to alcohols using a large excess of sodium borohydride in methanol. Some of the carboxylates are mono-unsaturated, in which cases the authors note reduction of the double bonds.

S. W. Chaikin and W. G. Brown, J. Am. Chem. Soc., volume 71, 122 (1949) disclose reduction of various aldehydes, ketones and acid chlorides using sodium borohydride. The authors report that olefinic double bonds of mono-unsaturated aldehydes and ketones were not reduced but that those of crotonyl chloride and cinnamoyl chloride were reduced.

J. Nikawa and T. Shiba, Chem. Letters, 981 (1979) describe reduction of 1-succinimidyl esters of various saturated carboxylic acids using sodium borohydride in tetrahydrofuran.

B. C. Subba Rao, Current Science, number 6, 218 (1961), report reduction of various methyl carboxylates, including crotonic acid, using a sodium borohydride-titanium (IV) chloride reagent. Reduction of crotonic, oleic and cinnamic acids, as free acids, resulted in saturated alcohols.

T. Koizumi et al., Chem. Pharm. Bull. (Japan), volume 21, number 2, 312 (1973) describe preparation of mixed carboxylic-diphenylphosphoric anhydrides by reacting carboxylic acids with diphenylphosphorochloridate in the presence of triethylamine in tetrahydrofuran, and reduction of the resulting mixed anhydrides using sodium borohydride. Cinnamic acid is the only unsaturated and nonaromatic acid reported.

K. Ishizumi et al., Chem. Pharm. Bull. (Japan), volume 16, number 3, 492 (1968) describe in situ preparation of acid anhydrides of several carboxylic acids and reduction of the anhydrides with sodium borohydride in aqueous tetrahydrofuran. Cinnamic acid is the only unsaturated and nonaromatic acid reported. The anhydrides were prepared by reacting the acids with ethyl chloroformate and triethylamine in tetrahydrofuran.

To date, there has not been a convenient, inexpensive process for preparing conjugated dienyl alcohols, herein referred to as conjugated dienols. There has not been a process for preparing conjugated dienols from activated acid esters. D. S. Tarbell and N. A. Leister, J. Org. Chem., volume 23, 1149 (1958) disclose mixed anhydrides prepared by reacting sorbic acid with ethyl chloroformate in the presence of triethylamine.

L. E. Overman et al., J. Org. Chem., volume 43, 2164 (1978), describe preparation of 1-N-acylamino-1,3-dienes from 2,4-pentadienoic acid or sorbic acid. The preparation proceeds through mixed anhydrides prepared by reacting the free acid with ethyl chloroformate in the presence of diisopropylethylamine or triethylamine; irreproducible results were obtained using the pentadienoic acid in the presence of triethylamine.

Fernholz et al., U.S. Pat. No. 3,468,948, disclose preparation of a sorbic acid anhydride by reacting the polyester of 3-hydroxy-4-hexenoic acid with a chloroformate in the presence of triethylamine.

Andrews, U.S. Pat. No. 4,293,674 discloses compounds prepared by transesterification of conjugated dienols and alkyl methacrylates, as well as homopolymers and copolymers of such compounds. Milligan et al., U.S. Pat. No. 3,520,839, disclose other uses for compounds derived from sorbyl alcohol including, for example, carbamate insecticides.

G. W. Anderson et al., J. Am. Chem. Soc., volume 86, 1839 (1964) report that N-hydroxysuccinimidyl esters of amino acids are more active towards peptidization. The -imide esters are prepared by reacting the free acid with N-hydroxysuccinimide in the presence of dicyclohexylcarbodiimide in tetrahydrofuran.

SUMMARY OF THE INVENTION

The invention resides in a process for preparing conjugated dienols which comprises contacting and reacting an activated ester of a conjugated dienoic acid, having the formula $R^1CR^2\!=\!CR^3CR^4\!=\!CHC(O)OY$, with an alkali metal borohydride at about $-5°$ to $35°$ C. for a time sufficient to effect reaction, wherein said formula, $R^1$ through $R^4$ are, independently, H, $C_{1-4}$ alkyl, or optionally substituted phenyl; Y is $X(O)(OR)_n$ or

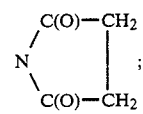

X is carbon or phosphorus and n is 1 when X is carbon and 2 when X is phosphorus.

The invention also resides in said process wherein the activated ester is prepared in situ by contacting and reacting a conjugated dienoic acid having the formula $R^1CR^2\!=\!CR^3CR^4\!=\!CH_2C(O)OH$ in a solvent with (i) a tertiary amine and a chloroester having the formula ClX(O)(OR)$_n$ nor (ii) N-hydroxysuccinimide and a N,N'-disubstituted carbodiimide, at about −15° to +25° C. wherein said formulae the variables are as defined above and the substituents of the carbodiimide are C$_{1-8}$ alkyl or cyclohexyl.

DETAILED DESCRIPTION OF THE INVENTION

Conjugated dienols are compounds having the formula R$^1$CR$^2$=CR$^3$CR$^4$=CHCH$_2$OH, wherein R$^1$ through R$^4$ are, independently, H, C$_{1-4}$ alkyl or optionally substituted phenyl. They are prepared, in accordance with this invention, by alkali borohydride reduction of an activated ester of a conjugated dienoic acid.

The reduction is carried out by adding excess borohydride, usually about 0.5 to 10 moles of borohydride, preferably 2 to 4 moles, per mole of ester. Preferably, water is added to dissolve the borohydride in the reaction mixture. The preferred borohydride is sodium borohydride.

The reduction can be carried out at about −5° to +35° C., preferably 0° to 10° C. Alkali borohydrides hydrolyze in water at temperatures above about 15° C., the rate of hydrolysis increasing with increase in temperature. To minimize reaction of by-product CO$_2$ with the borohydride, the pressure is preferably atmospheric or lower to facilitate rapid removal of the CO$_2$. Reaction time varies from about 0.25 to 12 hours. The reduction may be carried out by batch, semi-continuous or continuous procedures.

Borohydride reduction of the ester is advantageous because it is accomplished with low-cost reagents and does not require anhydrous conditions. A further advantage, it has now been found, is that the activated ester can be prepared in situ. This allows preparation of conjugated dienols from conjugated acids in a single two-step process, without need for isolation of the ester.

The ester can be a mixed anhydride having the formula R$^1$CR$^2$=CR$^3$CR$^4$=CHC(O)OY wherein R$^1$–R$^4$ are H, C$_{1-4}$ alkyl or optionally substituted phenyl; Y is X(O)(OR)$_n$; X is carbon or phosphorus, R is H, C$_{1-4}$ alkyl or optionally substituted phenyl and n is one when X is C and 2 when X is P. Alternatively, the ester can be an N-hydroxysuccinimidyl ester having the same formula except that Y is

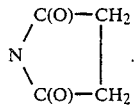

Preparation of the anhydride is carried out by contacting and reacting a conjugated dienoic acid with a tertiary amine and a chloroester having the formula ClX(O)(OR)$_n$ wherein X, R and n are as defined above. Preparation of the -imide ester is carried out by contacting and reacting such acid with N-hydroxysuccinimide and a N,N'-disubstituted carbodiimide wherein the carbodiimide substituents are cyclohexyl or C$_{1-8}$ alkyl.

Approximately equimolar amounts of the acid, chloroester and tertiary amine, or of the acid, -imide and -diimide, are admixed in a solvent at a total concentration of about 0.5 to 5M, preferably 0.5 to 1.5M. The concentration may be limited by the solubility of the reactants. Excessive amounts of any of the reactants are undesirable due to possible reaction with the borohydride upon addition of the borohydride to effect reduction.

Useful tertiary amines include cyclic and acylic tertiary amines which are basic and soluble in the reaction medium. Nonlimiting examples are: trimethylamine, triethylamine, N,N-diisopropylethylamine, N,N-dimethyl aniline, N,N-diethyl aniline, N,N-diethylcyclohexylamine, N,N-dimethylbenzylamine, N-ethyl morpholine, N-ethyl pyrrolidine, N-ethyl pyrrole, N-ethyl piperidine, N-methyl morpholine, N-methyl pyrrolidine, N-methyl pyrrole, N-methyl piperidine, 1,4-diazabicyclo[2.2.2]octane, 2-dimethylaminopyridine, 4-dimethylaminopyridine, N-methylimidazole, 1,5-diazabicyclo[4.3.0]non-5-ene, and 1,8-diazabicyclo[5.4.0]undec-7-ene. Triethylamine is preferred.

N,N'-dicyclohexyl carbodiimide is the preferred carbodiimide.

The activated ester preparation is carried out in the presence of a solvent at −15° to +25° C., preferably −8° to +10° C. Suitable solvents are organic liquids which are inert to the reactants in the ester preparation step and to the ester and the borohydride, and in which said reactants, ester and borohydride are soluble. The solvent is preferably miscible with water because of the desirability of adding water during the borohydride reduction. When an anhydride is prepared, the solvent is preferably a poor solvent for amine salts, such as triethylamine hydrochloride, which are by-products of that preparation. Alcohols which react with the activated esters and water-soluble ketones such as acetone which are reactive towards borohydrides should be avoided. If the process is to be carried out in the absence of water, liquid aromatic hydrocarbons such as toluene, and esters such as ethyl acetate may be used. Nonlimiting examples of other solvents are: tetrahydrofuran, dioxane, 1,2-dimethoxy ethane (glyme), diethylene glycol dimethyl ether (diglyme) and methylal. Preferred solvents are tetrahydrofuran, glyme and diglyme.

The preferred dienoic acids are 2,4-hexadienoic acid (sorbic acid), 5-phenyl-2,4-pentadienoic acid and piperic acid. These are commercially available. The preferred ester is the anhydride wherein Y is C(O)OC$_2$H$_5$, R$^1$ is CH$_3$, C$_6$H$_5$ or

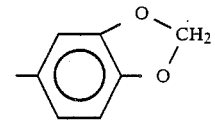

and R$^2$–R$^4$ are H.

Several experiments were carried out in which sorbic acid, its acid chloride or its methyl or ethyl ester was treated with sodium borohydride in the presence of a Lewis acid selected from TiCl$_4$, AlCl$_3$, LiCl, MgCl$_2$, LiBr and LiI, supported on alumina. In another experiment, sorboyl chloride was treated with sodium borohydride in the absence of a Lewis acid. In all cases, either no reaction occurred or no sorbyl alcohol was formed.

In the following illustrative examples, temperature is reported in degrees Celsius.

EXAMPLE 1

2,4-Hexadienol

Into a 500 mL, three-necked, round bottom flask equipped with a low temperature thermometer, addition funnel, nitrogen inlet connected to a bubbler and magnetic stir-bar were charged in order: 2,4-hexadienoic acid (11.21 g, 0.1 mole), tetrahydrofuran (THF, 150 mL) and triethylamine (14 mL, 10.16 g, 0.1 mole). The stirred solution was cooled to −5° in an ammonium chloride ice bath. Ethyl chloroformate (10.85 g, 0.1 mole) dissolved in THF (25 mL) was added over a 33 min period. After the addition was complete, the mixture was stirred for another 30 min at between −5° and 0° to complete preparation of the mixed carboxylic-carbonic anhydride. Triethylamine hydrochloride precipitated out and was removed by suction-filtration through a medium-pore size frit and washed with 50 mL of THF. The washings were combined with the filtrate containing the mixed anhydride, and this solution was used in the next stage without purification or isolation.

Into a 1-liter, four-necked, round bottom flask equipped with a thermometer probe, mechanical stirrer, nitrogen inlet and addition funnel were charged in order: water (100 mL) and sodium borohydride (9.45 g, 0.25 moles). The stirred solution was cooled to about 7° in an ice bath. The solution containing the mixed anhydride was added dropwise with vigorous stirring at a rate such that the temperature did not exceed 15°–17°. Copious evolution of carbon dioxide and formation of a white precipitate were observed. After addition of the mixed anhydride was complete, the cooling bath was removed and the reaction was allowed to proceed at ambient temperature (about 20° to 25°) for 3.5 h. Then, with cooling in an ice bath, concentrated hydrochloric acid (20 mL) was added dropwise, resulting in the formation of an aqueous phase and an organic phase, which were separated. The aqueous phase was extracted once with 200 mL of diethyl ether followed by a second extraction with 100 mL of the same. The combined organic phase and ether extracts were washed excessively with 10% aqueous sodium hydroxide (50 mL), water (50 mL) and brine (50 mL). The organic phase was dried over anhydrous sodium sulfate. After filtration, solvent was removed on a rotary evaporator at reduced pressure. This gave 8.879 (92%) of a pale yellow liquid. Gas chromatographic analysis (GC) (10% SP-2100, a silicone-based liquid; 10'×⅛" (3 m×3 mm) stainless steel column; 65°–220° C. at 15°/min) showed a single major peak (95%) corresponding to 2,4-hexadienol. A nuclear magnetic resonance (NMR) spectrum of the material was identical to a pure reference sample of 2,4-hexadienol. Short-path distillation gave 5.60 g (58%) of the dienol, b.p. 60°–64° C./5–6 mmHg (7–8 Pa).

EXAMPLE 2

2,4-Hexadienol

The procedure of Example 1 was substantially followed with the following significant modifications: (i) in the reduction step, the amount of sodium borohydride was reduced to 3.80 g, 0.10 mole; (ii) the amount of water used in the reduction was reduced to 40 mL; (iii) the reduction was allowed to proceed for 4.75 h at ambient temperature (20° to 25°) after addition of the mixed anhydride to the aqueous borohydride was complete. Work-up and, after one week on a bench top, short-path distillation gave 1.31 g (12%) of 2,4-hexadienal, b.p. 46° C./0.2 mmHg (0.3 Pa). The amount of undistilled residue was 7.50 g, indicating that product should be distilled promptly.

EXAMPLE 3

2,4-Hexadienol

The procedure of Example 1 was substantially followed with the following significant modifications: (i) N,N-diisopropylethylamine (17.5 mL, 12.98 g, 0.1 mole) was substituted for triethylamine; (ii) mixed anhydride formation was conducted at 6°–8°; (iii) the reduction with sodium borohydride was conducted at ambient temperature (24°–32° C.) without external cooling. Work-up and short-path distillation gave 3.4 g (35%) of a clear colorless liquid (b.p. 46°–42° C./1.2–1.0 mmHg, 1.6–1.3 Pa) which partially crystallized on standing. Analysis by thin-layer chromatography (TLC) and NMR showed the product to be sorbyl alcohol containing traces of aldehyde and aliphatic material. Some product may have been lost by evaporation during distillation.

EXAMPLE 4

2,4-Hexadienol

The procedure of Example 1 was substantially followed with the following significant modifications: (i) dipheny chlorophosphate (26.86 g, 0.1 mole) was substituted for ethyl chloroformate and was dissolved in THF (75 mL); (ii) formation of the mixed carboyxlic-phosphoric anhydride was conducted at 10° or lower and allowed to run for 2 h; (iii) the reduction with sodium borohydride (9.45 g, 0.1 mole in 80 mL water) was conducted at ambient temperature (20°–35° C.) initially and then with cooling between 20°–24° C. over a total of three hours. Work-up and short-path distillation gave 3.29 g (33.6%) of a clear colorless liquid, b.p. 36° C./0.3–0.4 mmHg (0.4–0.5 Pa) that partially crystallized on standing. Analysis by TLC, NMR and GC/MS showed it to be mostly sorbyl alcohol containing traces of triethylamine and cis- and trans-3-hexenol.

EXAMPLE 5

2,4-Hexadienol

Sorbic acid 1-succinimidyl ester was prepared substantially by the procedure described by G. W. Anderson et al., J. Am. Chem. Soc., volume 86, 1839 (1964), sorbic acid being substituted for the amino acids employed therein, as described below.

A 500 mL, round bottom flask equipped with a thermometer probe, a magnetic stir-bar and nitrogen inlet were charged, in order: N-hydroxysuccinimide (18.80 g, 0.1623 mole), 2,4-hexadienoic acid (18.31 g, 0.1623 mole) and tetrahydrofuran (250 mL). The mixture, in an ice bath, was stirred under nitrogen while dicyclohexylcarbodiimide (36 g, 0.1744 mole) was added, followed by addition of tetrahydrofuran (40 to 50 mL). TLC indicated presence of sorbic acid after about 6 h stirring at ambient temperature (20°–25°). After stirring for about 22 h at ambient temperature, white dicyclohexylurea was filtered and washed with tetrahydrofuran (3×50 mL). Solvent was removed from the combined filtrate and washings in a rotary evaporator. Since TLC indicated presence of sorbic acid in the product, an off-white solid, the product was dissolved in an ether-ethyl acetate mixture, washed with 5–10% potassium carbonate (6×50 mL), dried over anhydrous sodium sulfate, filtered and stripped, yielding 31 g of an off-white solid. The solid was dissolved in hot isopropanol (120–130 mL), and left to stand at room temperature overnight to recrystallize. The mixture was suction filtered. The residue was washed with isopropanol (2×20 mL) and oven dried at about 50° C. for 4 to 5 h, yielding 29.2 g of a solid containing sorbic acid-1-succinimidyl ester, mp 100°-102° C., 86% yield.

Sorbyl alcohol was prepared from the above-prepared ester as follows:

A 500 mL, four-necked, round bottom flask equipped with a nitrogen inlet, paddle stirrer, thermometer probe and addition funnel was charged with sodium borohydride (9.45 g, 0.25 mole) dissolved in water (80 mL). Into the addition funnel was charged a solution of the sorbic acid 1-succinimidyl ester (20.92 g, 0.1 mole) in tetrahydrofuran (150 mL). With vigorous stirring under a nitrogen atmosphere, the solution of succinimidyl ester was added dropwise over 50 min at ambient temperature (20°-25°). Stirring was continued for another 6 h. Concentrated hydrochloric acid (20 mL) was then carefully added, dropwise. The resulting mixture was extracted in ether (2×150 mL), and the combined extracts were washed successively with 10% aqueous potassium carbonate (3×70 mL) and water (100 mL), dried over anhydrous sodium sulfate and filtered. Solvent removal under vacuum gave 3.2 g of a white solid. Analysis by TLC (silica gel, 98:2 v/v methylene chloride/isopropanol) and NMR showed the presence of sorbyl alcohol.

EXAMPLE 6

2,4-Pentadienol

The procedure of Example 1 was substantially followed with the following significant modifications: (i) a 1-liter four-necked, round bottom flask was used in the mixed anhydride step with 2,4-pentadienoic acid (29.43 g, 0.3 mole), THF (450 mL), triethylamine (52 mL, 30.48 g, 0.3 mole) ethyl chloroformate (32.55 g, 0.3 mole) in THF (75 mL); (ii) the precipitated triethylamine hydrochloride filter cake was washed three times with THF (50 mL); (iii) in the reduction step a 3-liter, four necked, round bottom flask was charged with water (3000 mL) and sodium borohydride (28.35 g, 0.75 mole). Work-up and short-path distillation gave 7.92 g (31.4%) of 2,4-pentadienol, a clear, colorless liquid, b.p. 58°-62° C./11 mmHg (15 Pa). The boiling point, infrared and NMR spectra of this material were consistent with the data for 2,4-pentadienol reported by Schneider et al., J. Am. Chem. Soc., volume 102, 6114 (1980) and K. Mori, Tetrahedron Letters, volume 30, 3807 (1974). IR (film: 3350, 1604. 90 MHz 'H NMR: δ3.12 (br s, 1H, exchangeable with D₂O, OH),

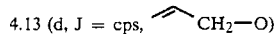

4.13 (d, J = cps, CH₂—O)

5.03-6.56 (complex m, 5H, CH=C).

EXAMPLE 7

5-Phenyl-2,4-Pentadienol

The procedure of Example 1 was substantially followed using 5-phenyl-2,4-pentadienoic acid (22.65 g, 0.13 mole), THF (195 mL), triethylamine (18.2 mL, 13.21 g, 0.13 mole) and ethyl chloroformate (14.1 g, 0.13 mole) dissolved in THF (39 mL). The ethyl chloroformate solution was added at a temperature in the range 0° to 10° C. The resulting mixed anhydride was reduced with sodium borohydride (12.28 g, 0.13 mole) in water (130 mL). Work-up and removal of the organic solvent at reduced pressure in a rotary evaporator yielded 19.4 g of an off-white solid. Trituration of this material gave 18.9 g (86.4%) of a white powder, m.p. 79.5°-81.5° C. TLC (silica gel, 96:4 v/v methylene chloride-isopropanol) showed one major spot of Rf 0.61 corresponding to 5-phenyl-2,4-pentadienol, with little or no trace of starting material. 80 MHz 'H NMR: δ3.05 (br s, 0.375 H, exchangeable with D₂O), 3.97 (br doublet, J=5.3 Hz, 0.625 H, exchangeable with D₂O), 4.17 (d, J=5.3 Hz, 2H, C=C—CH₂—O), 5.80-7.50 (complex m, 9H Ar-H and CH=C).

Analysis by GC and MS showed the major component to have m/e 160. Minor impurities included benzaldehyde and cinnamaldehyde. IR (CHCl₃): cm⁻¹ 3620 (s), 3430 (br, OH), 3020 (s), 1650 (m), 1620 (m), 1600 (m).

INDUSTRIAL APPLICABILITY

The process of the invention is useful for preparing conjugated dienols which, as disclosed in U.S. Pat. No. 4,293,674, Andrews, provide cure sites for air-drying acrylic coating compositions. Sorbyl alcohol is used industrially for said purpose as a component of acrylic finishes for automobiles and other metallic objects.

BEST MODE

The best mode for carrying out the invention is illustrated by Examples 1, 6 and 7.

Although the above description illustrates the preferred embodiments of the invention, the invention is not limited to the precise embodiments herein disclosed.

I claim:

1. Process for preparing the conjugated dienol having the formula R¹CR²=CR³CR⁴=CHCH₂OH which comprises contacting and reacting an activated conjugated dienoic acid ester having the formula R¹CR²=CR³CR⁴=CHC(O)OY, with an alkali metal borohydride at about −5° to +35° C. for a time sufficient to effect reaction, wherein said formulae R¹-R⁴ are, independently, H, C₁₋₄ alkyl, or optionally substituted phenyl, Y is X(O)(OR)ₙ or

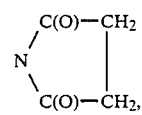

X is carbon or phosphorus, R is H, C₁₋₄ alkyl or optionally substituted phenyl and n is 1 when X is carbon and 2 when X is phosphorus.

2. Process of claim 1 wherein the activated conjugated dienoic acid ester is prepared in situ by contacting and reacting the conjugated dienoic acid having the formula R¹CR²=CR³CR⁴CH₂CO₂H in a solvent with a tertiary amine and a chloroester having the formula ClX(O)(OR)ₙ, at about −15° to +25° C.

3. Process of claim 1 wherein Y is C(O)OC₂H₅, R¹ is CH₃, C₆H₅ or

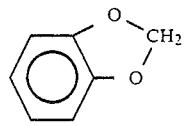

and R²-R⁴ are H.

4. Process of claim 1 wherein the alkali borohydride is sodium borohydride and the amount of the borohydride is about 0.5 to 10 moles per mole of ester.

5. Process of claim 2 wherein the alkali borohydride is sodium borohydride, the amount of the borohydride is about 0.5 to 10 moles per mole of ester and the solvent is miscible with water.

6. Process of claim 1 wherein the activated conjugated dienoic acid ester is prepared in situ by contacting and reacting the conjugated dienoic acid having the formula $R^1CR^2{=}CR^3CR^4CH_2CO_2H$ in a solvent with N-hydroxysuccinimide and a N,N'-disubstituted carbodiimide wherein the substituents of the carbodiimide are $C_{1-8}$ alkyl or cyclohexyl.

7. Process of claim 3 wherein the borohydride is sodium borohydride and the amount of borohydride is 0.5 to 10 moles per mole of ester and sufficient water is added to dissolve the borohydride in the reaction mixture.

8. Process of claim 4 wherein the amount of borohydride is 2 to 4 moles per mole of ester and the temperature is 0° to 10° C.

9. Process of claim 5 wherein the temperature during preparation of the ester is −8° to +10° C. and, during reduction, 0° to 10° C. and the amount of borohydride is 2 to 4 moles per mole of ester.

10. Process of claim 2 wherein Y is $C(O)OC_2H_5$, $R^1$ is $CH_3$, $C_6H_5$ or

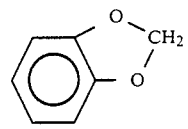

and $R^2$-$R^4$ are H.

11. Process of claim 6 wherein the carbodiimide is N,N'-dicyclohexyl carbodiimide.

12. Process of claim 7 wherein the temperature is 0° to 10° C. and the amount of borohydride is 2 to 4 moles per mole of ester.

13. Process of claim 10 wherein the borohydride is sodium borohydride and the amount of borohydride is 0.5 to 10 moles per mole of ester.

14. Process of claim 11 wherein the borohydride is sodium borohydride and the amount of borohydride is 0.5 to 10 moles per mole of ester.

15. Process of claim 10 wherein the temperature during preparation of the ester is −8° to +10° C. and, during reduction, 0° to 10° C. and the amount of borohydride is 2 to 4 moles per mole of ester.

16. Process of claim 11 wherein the temperature during preparation of the ester is −8° to +10° C. and, during reduction, 0° to 10° C. and the amount of borohydride is 2 to 4 moles per mole of ester.

17. Process of claim 15 wherein the solvent is tetrahydrofuran, glyme or diglyme.

18. Process of claim 16 wherein the solvent is tetrahydrofuran, glyme or diglyme.

* * * * *

UNITED STATES PATENT AND TRADEMARK OFFICE
CERTIFICATE OF CORRECTION

PATENT NO. : 4,526,993

DATED : July 2, 1985

INVENTOR(S) : Chaucer C. Tang

It is certified that error appears in the above—identified patent and that said Letters Patent is hereby corrected as shown below:

Column 3, line 1, "nor" should read --or--.

Column 7, line 53, "J=cps" should read --J=6 cps--.

Column 8, line 52, cancel beginning with "2. Process of Claim 1" to and including "at about -15° to +25°C." in column 8, line 57, and insert the following claim:

Claim 2. Process of Claim 1 wherein the activated conjugated dienoic acid ester is prepared in situ by contacting and reacting the conjugated dienoic acid having the formula $R^1CR^2=CR^3CR^4CH_2CO_2H$ in an inert organic solvent with a tertiary amine and a chloroester having the formula $ClX(O)(OR)_n$, at about -15 to +25°C, wherein R is H, $C_{1-4}$ alkyl or optionally substituted phenyl, and X is carbon or phosphorus.

Column 9, line 9, cancel beginning with "6. Process of Claim 1" to and including "$C_{1-8}$ alkyl or cyclohexyl." in column 9, line 15, and insert the following claim:

Claim 6. Process of Claim 1 wherein the activated conjugated dienoic acid ester is

UNITED STATES PATENT AND TRADEMARK OFFICE
CERTIFICATE OF CORRECTION

PATENT NO. : 4,526,993
DATED : July 2, 1985
INVENTOR(S) : Chaucer C. Tang

It is certified that error appears in the above—identified patent and that said Letters Patent is hereby corrected as shown below:

prepared in situ by contacting and reacting the conjugated dienoic acid having the formula $R^1CR^2=CR^3CR^4CH_2CO_2H$ in an inert organic solvent with N-hydroxysuccinimide and a N,N'-disubstituted carbodiimide wherein the substituents of the carbodiimide are $C_{1-8}$ alkyl or cyclohexyl.

Signed and Sealed this

Third Day of March, 1987

Attest:

DONALD J. QUIGG

Attesting Officer

Commissioner of Patents and Trademarks